(12) United States Patent
O'Reilly et al.

(10) Patent No.: US 6,800,101 B2
(45) Date of Patent: Oct. 5, 2004

(54) DEACTIVATABLE BIOCIDES FOR HYDROCARBONACEOUS PRODUCTS

(75) Inventors: Kirk T. O'Reilly, El Sobrante, CA (US); Michael E. Moir, San Rafael, CA (US); Dennis J. O'Rear, Petaluma, CA (US)

(73) Assignee: Chevron U.S.A. Inc., Sa Ramon, CA (US)

( * ) Notice: Subject to any disclaimer, the term of this patent is extended or adjusted under 35 U.S.C. 154(b) by 0 days.

(21) Appl. No.: 09/982,699

(22) Filed: Oct. 18, 2001

(65) Prior Publication Data

US 2003/0162845 A1 Aug. 28, 2003

(51) Int. Cl.$^7$ .............................. C10L 1/10; C10L 1/18; C10L 1/22

(52) U.S. Cl. ............................. 44/300; 44/412; 44/434; 44/437; 44/451; 585/14; 518/700; 518/711

(58) Field of Search .......................... 44/437, 451, 412, 44/434, 300; 585/14; 518/700, 711

(56) References Cited

U.S. PATENT DOCUMENTS

| | | | |
|---|---|---|---|
| 3,393,058 A | | 7/1968 | Oppermann |
| 4,086,066 A | | 4/1978 | McDermott |
| 4,185,094 A | * | 1/1980 | Crump ..................... 106/18.29 |
| 4,188,380 A | | 2/1980 | Oswald |
| 4,507,517 A | | 3/1985 | Devries et al. |
| 4,599,474 A | | 7/1986 | Devries et al. |
| 4,704,487 A | | 11/1987 | Devries et al. |
| 4,704,493 A | | 11/1987 | Devries et al. |
| 4,708,720 A | * | 11/1987 | Grangette et al. ............ 44/301 |
| 4,709,108 A | | 11/1987 | Devries et al. |
| 4,734,537 A | | 3/1988 | Devries et al. |
| 4,814,533 A | | 3/1989 | Devries et al. |
| 4,814,534 A | | 3/1989 | Devries et al. |
| 4,814,538 A | | 3/1989 | Devries et al. |
| 4,853,140 A | | 8/1989 | Payne et al. |
| 4,867,757 A | | 9/1989 | Payne |
| 5,055,325 A | | 10/1991 | Trivett |
| 5,382,739 A | | 1/1995 | Atkins et al. |
| 5,416,210 A | | 5/1995 | Sherba et al. |
| 5,433,863 A | | 7/1995 | Braden et al. |
| 6,059,955 A | | 5/2000 | Cody et al. |
| 6,069,142 A | | 5/2000 | Gaffney et al. |

FOREIGN PATENT DOCUMENTS

| | | |
|---|---|---|
| EP | 0609079 A1 | 8/1994 |
| EP | 0921184 A1 | 6/1999 |
| WO | WO 00/20534 A1 | 4/2000 |

OTHER PUBLICATIONS

Bolch, C.J., et al., *Chemical and Physical Treatment Options to Kill Toxic Dinoflagellate Cysts in Ships' Ballast Water, J. Marine Env. Engg.*, vol. 1, 1993, pp. 23–29, Gordon and Breach Science Publishers, US.

Carey, F.A., et al., *Advanced Organic Chemistry, Chapter 2: Reactions of Carbon Nucleophiles with Carbonyl Groups The Mannich Reaction*, $2^{nd}$ edition, 1983, pp. 59–62. Plenum Press, New York.

Carlton, J.T., et al., *Shipping Study: The Role of Shipping in the Introduction of Nonindigenous Aquatic Organisms to the Coastal Waters of the United States (other than the Great Lakes) and an Analysis of Control Options, The National Sea Grant College Program/Connecticutt Sea Grant Project R/ES–6*, Report No. CG–D–11–95, Apr. 1995, National Technical Information Service, Springfield, VA.

Morrison, R.T., et al., *Organic Chemistry*, $2^{nd}$ edition, 1966, pp. 631–632, Allyn and Bacon, Inc., Boston.

Prior, S.D., et al., *Acetylene as a suicide substrate and active site probe for methane monooxygenase from Methylococcus capsulatus (Bath), Federation of European Microbiological Societies: Microbiology Letters*, vol. 29, 1985, pp. 105–109, Elsevier/North Holland, Amsterdam.

Roets, Piet, et al., *Stability and Handling of SASOL Semi-Synthetic Jet Fuel*, $6^{th}$ International Conference on Stability and Handling of Liquid Fuels, Vancouver, B.C., Canada, Oct. 13–17, 1997, pp 798–804, Publisher National Technical Information Services, Springfield, Virginia.

Stirling, D.I., et al., *Effect of Metal–Binding Agents and Other Compounds on Methane Oxidatin by Two Strains of Methyloccoccus capsulatus, Archives of Microbiology*, vol. 114, 1977, pp. 71–76, Springer–Verlag.

Yeager, C.M., et al., *Inactivation of Toluene 2–Monooxygenase in Burkholderia cepacia G4 by Alkynes, Applied & Environmental Microbiology*, vol. 65, No. 2, Feb. 1999, pp. 632–639, American Society for Microbiology.

De Montellano, P.R., et al., *Self–catalyzed Inactivation of Hepatic Cytochrome P–450 by Ethynyl, The Journal of Biological Chemistry*, vol. 255, No. 12, Jun. 25, 1980, pp. 5578–5585, American Society for Biochemistry and Molecular Biology, Baltimore, MD.

De Montellano, P.R., *Alkenes, and Alkynes, Bioactivation of Foreign Compounds*, Chapter 5, 1985, pp. 121–155, Academic Press, Inc., New York.

*Global spread of microorganisms by ships, Brief Communications*, Nature, Nov. 2, 2000.

(List continued on next page.)

*Primary Examiner*—Cephia D. Toomer
(74) *Attorney, Agent, or Firm*—Burns, Doane, Swecker & Mathis, L.L.P.

(57) ABSTRACT

The present invention relates to the use of deactivatable biocides for hydrocarbonaceous products, in particular, rapidly biodegradable hydrocarbonaceous products. The present invention also relates to methods of inhibiting growth and reproduction of microorganisms in hydrocarbonaceous products, in particular, in rapidly biodegradable hydrocarbonaceous products, containing minor amounts of aqueous liquids. The deactivatable biocides of the present invention may be derived from a Fischer-Tropsch process.

35 Claims, No Drawings

OTHER PUBLICATIONS

Glutaraldehyde: The Right Biocide for Many Environments, *Union Carbide Corporation,* 1999 Published by Union Carbide, Danbury CT.

Grab, L.A., et al., *Comparative Biocidal Efficacy vs Sulfate–Reducing Bacteria, Materials Performance,* vol. 32, No. 6, 1993, pp. 59–62, National Association of Corrosion Engineers, Houston, TX.

Hudgins, C.M., Jr., *Chemical Treatments and Usage in Offshore Oil and Gas Production Systems, Journal of Petroleum Technology,* vol. 44, No. 5, May 1992, pp. 604–611, Society of Petroleum Engineers, Richardson, TX.

Hyman, M.R., et al., *Acetylene Inhibion of Metalloenzymes, Analytical Biochemistry,* vol. 173, No. 2, 1988, pp. 207–220, Academic Press, Inc., New York.

Leung, Hon–Wing, *Ecotoxicology of Glutaraldehyde: Review of Environmental Fate and Effects Studies, Ecotoxicology and Environmental Safety,* 49, 26–39, 2001, Section B, pp 26–39, Academic Press.

*Methods for Measuring the Acute Toxicity of Effluents and Receiving Waters to Freshwater and Marine Organisms,* $4^{th}$ Edition, EPA/600/4–90/027F, Aug. 1993, United States Environmental Protection Agency, Reproduced by: National Technical Information Service, U.S. Dept. of Commerce, Springfield, VA.

U.S. patent application No. 09/982,701, O'Reilly, et al., *Deactivatable Biocides in Ballast Water,* filed on Oct. 18, 2001, attorney docket No. 005950–715.

U.S. patent application No. 09/982,702, O'Reilly, et al., *Process for Disposing Biocide–Containing Cooling Water,* filed on Oct. 18, 2001, attorney docket No. 005950–714.

U.S. patent application No. 09/982,714, O'Reilly, et al., *Inhibition of Biological Degradation in Fischer–Tropsch Products,* filed on Oct. 18, 2001, attorney docket No. 005950–696.

\* cited by examiner

DEACTIVATABLE BIOCIDES FOR HYDROCARBONACEOUS PRODUCTS

FIELD OF THE INVENTION

The present invention relates to the use of deactivatable biocides for hydrocarbonaceous products, in particular, rapidly biodegradable hydrocarbonaceous products. The present invention also relates to methods of inhibiting growth and reproduction of microorganisms in hydrocarbonaceous products, in particular, in rapidly biodegradable hydrocarbonaceous products, containing minor amounts of aqueous liquids.

BACKGROUND OF THE INVENTION

Certain microbiological problems may arise with respect to the storage and transportation of hydrocarbonaceous products. Hydrocarbons can act as a nutrient for microorganisms; therefore, hydrocarbonaceous products (i.e., fuels such as jet fuel, diesel fuel, naphtha, lubes, and solvents) can be attacked by microorganisms. Microorganisms can slowly grow at the boundary layers of the hydrocarbonaceous product and air, and can grow more rapidly if the hydrocarbonaceous product is also exposed to a layer of water.

Hydrocarbonaceous products are frequently exposed to a layer of water when stored in large storage vessels, such as storage tanks, fuel tanks of aircraft and holds of tankers. In these large storage vessels, water invariably forms due to condensation or it is initially present in the stored hydrocarbonaceous product and slowly separates therefrom. This water gradually forms a layer in the bottom of the storage vessels. The water layer forms an interface with the hydrocarbonaceous product, and becomes a breeding ground for a wide variety of microorganisms. These microorganisms utilize the hydrocarbonaceous product as a nutrient and can multiply.

Eventually the microorganisms can consume a large portion of the hydrocarbonaceous product. The extent to which the microorganisms consume the product is known as the extent of biodegradation, or the biodegradability of the product.

The microorganisms or microbes will grow mostly in the water phase, but when the hydrocarbonaceous product is disturbed during pumping or mixing, the microbes can be dispersed into the hydrocarbonaceous product and cause contamination. When present in the hydrocarbonaceous product, microbial growth can present a problem for several reasons. For example, hydrocarbonaceous products may become contaminated with microbes during storage or shipment and as a result of the microbes, become hazy or cloudy. The growing microorganisms may form sludge in the contaminated hydrocarbonaceous product. When contaminated hydrocarbonaceous products are used in an engine or equipment, the microbes and/or the sludge may decrease the efficiency of the engine or equipment or prevent it from functioning altogether, for example, by plugging filters. In addition, growth of microorganisms, in particular anaerobic sulfate reducing bacteria, in hydrocarbonaceous products during storage or transport may create corrosive sulfur-containing acids and damage the vessels in which the products are contained. This corrosion damage may lead to the need for eventual replacement of these large, expensive vessels.

Further, transport of hydrocarbonaceous products and/or a water layer contaminated with microbes creates a dispersal mechanism for human pathogens, waterborne diseases of plants and animals, and foreign organisms into the environment. For example, infectious bacteria such as cholera have been found in ballast water from marine tankers ("Global Spread of Microorganisms By Ships," *Brief Communications* Nov. 2, 2000 issue of Nature). These infectious organisms can create both a human health problem, and a health problem to native species in the receiving country. Water can also be the vehicle for the introduction of foreign higher life forms into the receiving countries' environment. By this route, Zebra clams are believed to have been introduced into the San Francisco Bay region.

There is a need for appropriate biocides for rapidly biodegradable hydrocarbonaceous products and methods of inhibiting the growth and reproduction of microorganisms in rapidly biodegradable hydrocarbonaceous products containing minor amounts of aqueous liquids. There is also a need for biocides for all hydrocarbonaceous products and methods of inhibiting growth and reproduction of microorganisms in hydrocarbonaceous products in which the biocide can be deactivated or neutralized after the period in which biological growth is expected to minimize potential environmental damage.

SUMMARY OF THE INVENTION

The invention relates to the use of deactivatable biocides for hydrocarbonaceous products, in particular, rapidly biodegradable hydrocarbonaceous products. These deactivatable biocides can be deactivated or neutralized after the period in which biological growth is expected to minimize potential environmental damage.

One aspect of the present invention is a biologically inhibited hydrocarbonaceous product comprising: a) a hydrocarbonaceous product subject to biological growth; and b) an effective amount of a deactivatable biocide to resist visible growth of microorganisms for at least 10 days under ambient conditions when exposed to a certified inoculant. The deactivatable biocide is deactivated or neutralized after the period in which biological growth is expected. Deactivation of the biocide minimizes environmental damage when the product, or streams that come in contact with the product, are introduced into the environment. The deactivatable biocide is irreversibly deactivated, i.e. the deactivable biocide does not re-generate to become active upon release to the environment.

The hydrocarbonaceous product may be a rapidly biodegradable hydrocarbonaceous product. The rapidly biodegradable hydrocarbonaceous product may be, for example, a Fischer-Tropsch-derived liquid product; a product derived from petroleum, diesel fuel, solvent, jet fuel, naphtha, lube base stock, lube base stock feedstock, or synthetic crude; or mixtures thereof. Preferably the product is a Fischer-Tropsch-derived liquid product. When the product is a Fischer-Tropsch-derived liquid product, the Fischer-Tropsch product preferably has a branching index of less than five.

An additional aspect of the present invention is a method of inhibiting the growth and reproduction of microorganisms in hydrocarbonaceous products containing minor amounts of aqueous liquids. In this method a hydrocarbonaceous product is provided. To the hydrocarbonaceous product is added an effective amount of a deactivatable biocide to resist visible growth of microorganisms for at least 10 days under ambient conditions when exposed to a certified inoculant. After the period in which growth and reproduction of microorganisms is expected, an effective amount of a neutralizing agent is added to deactivate the biocide. Deactivation of the biocide minimizes environmental damage when the product, or streams that come in contact with the product, are introduced into the environment. The biocide may be deactivated before the hydrocarbonaceous product and aqueous phase have been separated or after the hydrocarbonaceous product and aqueous layer have been separated. The deactivatable biocide is irreversibly deactivated, i.e. the deactivable biocide does not re-generate to become active upon release to the environment.

The hydrocarbonaceous product may be a rapidly biodegradable hydrocarbonaceous product. The rapidly biodegradable hydrocarbonaceous product may be, for example, a Fischer-Tropsch-derived liquid product; a product derived from petroleum, diesel fuel, solvent, jet fuel, naphtha, lube base stock, lube base stock feedstock, or synthetic crude; or mixtures thereof. Preferably the product is a Fischer-Tropsch-derived liquid product. When the product is a Fischer-Tropsch-derived liquid product, the Fischer-Tropsch product preferably has a branching index of less than five. When the product is a Fischer-Tropsch-derived liquid product, the deactivatable biocide is preferably a Fischer-Tropsch-derived deactivatable biocide.

A further aspect of the present invention is a method of inhibiting the growth and reproduction of microorganisms in Fischer-Tropsch-derived liquid products, preferably Fischer-Tropsch-derived liquid products having a branching index of less than five, containing minor amounts of aqueous liquids. This method comprises performing a Fischer-Tropsch synthesis process and isolating Fischer-Tropsch-derived liquid products from the Fischer-Tropsch process. To the Fischer-Tropsch derived liquid products is added an effective amount of a deactivatable biocide to resist visible growth of microorganisms for at least 10 days under ambient conditions when exposed to a certified inoculant. After the period in which growth and reproduction of microorganisms is expected, an effective amount of a neutralizing agent is added to deactivate the biocide.

The deactivatable biocide is preferably a Fischer-Tropsch-derived deactivatable biocide. If the biocide is a Fischer-Tropsch-derived deactivatable biocide, the method may also comprise the steps of synthesizing the Fischer-Tropsch-derived deactivatable biocide during the Fischer-Tropsch process and isolating both the Fischer-Tropsch-derived liquid products and the Fischer-Tropsch-derived deactivatable biocide. The deactivatable biocide is irreversibly deactivated.

Definitions:

Unless otherwise stated, the following terms used in the specification and claims have the meanings given below:

"Biocide" means any substance that kills or inhibits the growth of microorganisms, such as for example, bacteria, molds, slimes, fungi, and the like.

"Syngas" is a mixture that includes hydrogen and carbon monoxide. In addition to these species, others may also be present, including, for example, water, carbon dioxide, unconverted light hydrocarbon feedstock, and various impurities.

"Integrated process" means a process comprising a sequence of steps, some of which may be parallel to other steps in the process, but which are interrelated or somehow dependent upon either earlier or later steps in the total process.

"Branching index" means a numerical index for measuring the average number of side chains attached to a main chain of a compound. For example, a compound that has a branching index of two means a compound having a straight chain main chain with an average of approximately two side chains attached thereto. The branching index of a product of the present invention may be determined as follows. The total number of carbon atoms per molecule is determined. A preferred method for making this determination is to estimate the total number of carbon atoms from the molecular weight. A preferred method for determining the molecular weight is Vapor Pressure Osmometry following ASTM D-2503, provided that the vapor pressure of the sample inside the Osmometer at 45° C. is less than the vapor pressure of toluene. For samples with vapor pressures greater than toluene, the molecular weight is preferably measured by benzene freezing point depression. Commercial instruments to measure molecular weight by freezing point depression are manufactured by Knauer. ASTM D-2889 may be used to determine vapor pressure. Alternatively, molecular weight may be determined from an ASTM D-2887 or ASTM D-86 distillation by correlations which compare the boiling points of known n-paraffin standards.

The fraction of carbon atoms contributing to each branching type is based on the methyl resonances in the carbon NMR spectrum and uses a determination or estimation of the number of carbons per molecule. The area counts per carbon is determined by dividing the total carbon area by the number of carbons per molecule. Defining the area counts per carbon as "A", the contribution for the individual branching types is as follows, where each of the areas is divided by area A:

2–branches=half the area of methyls at 22.5 ppm/A
3–branches=either the area of 19.1 ppm or the area at 11.4 ppm (but not both)/A
4–branches=area of double peaks near 14.0 ppm/A
4+branches=area of 19.6 ppm/A minus the 4–branches
internal ethyl branches=area of 10.8 ppm/A The total branches per molecule (i.e. the branching index) is the sum of areas above.

For this determination, the NMR spectrum is acquired under the following quantitative conditions: 45 degree pulse every 10.8 seconds, decoupler gated on during 0.8 sec acquisition. A decoupler duty cycle of 7.4% has been found to be low enough to keep unequal Overhauser effects from making a difference in resonance intensity.

In a specific example, the molecular weight of a Fischer Tropsch Diesel Fuel sample, based on the 50% point of 478° F. and the API gravity of 52.3, was calculated to be 240. For a paraffin with a chemical formula $C_nH_{2n+2}$, this molecular weight corresponds to an average number n of 17.

The NMR spectrum acquired as described above had the following characteristic areas:

2–branches=half the area of methyl at 22.5 ppm/A=0.30
3–branches=area of 19.1 ppm or 11.4 ppm not both/A= 0.28
4–branches=area of double peaks near 14.0 ppm/A=0.32
4+branches=area of 19.6 ppm/A minus the 4–branches= 0.14
internal ethyl branches=area of 10.8 ppm/A=0.21

The branching index of this sample was found to be 1.25.

"Deactivatable biocide" means any biocide that can be deactivated or neutralized once the danger of microbial growth has ended. Deactivated or neutralized means that the biocide is no longer capable of killing or inhibiting the growth of microorganisms to any significant degree. Therefore, a deactivated biocide may be released into the environment with significantly reduced environmental risk. According to the present invention, the deactivatable biocide is irreversibly deactivated, i.e. the deactivable biocide does not re-generate to become active upon release to the environment.

"Fischer-Tropsch-derived deactivatable biocide" means a deactivatable biocide that may be generated as one of the many potential products of the Fischer-Tropsch synthesis process or may be generated as a component of the wastewater of the Fischer-Tropsch process. Fischer-Tropsch-derived biocides include, for example alkynes, oxygenates, and the like, and mixtures thereof "Fischer-Tropsch-derived liquid products mean hydrocarbonaceous, liquid products derived from a Fischer-Tropsch process. Fischer-Tropsch-derived liquid products include, for example, Fischer-Tropsch naphtha, Fischer-Tropsch jet fuel, Fischer-Tropsch diesel fuel, Fischer-Tropsch solvent, Fischer-Tropsch lube base stock, Fischer-Tropsch lube base oil, Fischer-Tropsch lube base stock feedstock, and mixtures thereof.

"Heavy Fischer Tropsch product" means a product derived from a Fischer Tropsch process that boils above the range of commonly sold distillate fuels: naphtha, jet or diesel fuel. This means greater than 400° F., preferably greater than 550° F., and most preferably greater than 700° F. This stream may be converted to olefins by a thermal cracking process.

"Light Fischer Tropsch product" includes hydrocarbons boiling below about 700° F. (e.g., tail gases through middle distillates). It is largely in the $C_5$ to $C_{20}$ range with decreasing amount up to about $C_{30}$. The light product comprises paraffinic products with a significant portion of alcohols and olefins. In some cases the light product may comprise as much as 50%, and even higher, alcohols and olefins.

"Hydrocarbonaceous" means containing hydrogen and carbon atoms and potentially also containing heteroatoms, such as oxygen, sulfur, nitrogen, and the like.

"Hydrocarbonaceous Product" means any hydrocarbonaceous product, including both conventional hydrocarbonaceous products and those identified as rapidly biodegradable hydrocarbonaceous products. Hydrocarbonaceous products contain hydrogen and carbon atoms and may also contain heteroatoms, such as oxygen, sulfur, nitrogen, and the like. Conventional hydrocarbonaceous products include conventional petroleum products, for example, petroleum, diesel fuel, solvent, jet fuel, naphtha, lube base stock, lube base stock feedstock, and lube base oil "Neutralizing Agent" means any compounds or reaction conditions that may be used to react a deactivatable biocide or to complex a deactivatable biocide to destroy the biocide's antimicrobial activity. A neutralizing agent effectively deactivates a biocide, thus neutralizing the biocide's antimicrobial effectiveness. According to the present invention, the neutralizing agent irreversibly deactivates the deactivatable biocide, i.e. the deactivable biocide does not re-generate to become active upon release to the environment. Neutralizing agents may include, for example, nitrogen containing compounds, oxidation conditions, hydrogenation conditions, and the like.

"Organic Biocide" means any biocide containing hydrogen, carbon, and oxygen and not containing any significant degree of heteroatoms. Therefore, in an organic biocide sulfur, nitrogen, halogen, or metals may be present only as trace impurities. Organic biocides may include, for example, aldehydes (i.e., glutaraldehyde), alkynes (i.e., propargyl alcohol), and the like, and mixtures thereof.

"Oxygenates" mean hydrocarbon compounds containing oxygen, including, for example, alcohols, carboxylic acids, aldehydes, and the like.

"Paraffin" means any saturated hydrocarbon compound, i.e., an alkane with a chemical formula of $C_nH_{2n+2}$.

"Rapidly Biodegradable Hydrocarbonaceous Product" means a hydrocarbonaceous product in which visual growth of microorganisms occurs in approximately ten days or less. Rapidly biodegradable hydrocarbonaceous products may include, for example, Fischer-Tropsch-derived liquid products; low aromatics diesel fuel; products derived from petroleum, diesel fuel, solvent, jet fuel, naphtha, lube base stock, lube base oil, lube base stock feedstock, synthetic crude; and mixtures thereof. Rapidly biodegradable hydrocarbonaceous products of the present invention preferably are Fischer-Tropsch-derived liquid products.

DETAILED DESCRIPTION OF ILLUSTRATIVE EMBODIMENTS

Hydrocarbonaceous products are typically stored or transported for a period of time before use, generally at least ten days. During storage and/or transport, minor amounts of aqueous liquids invariably form due to condensation or are initially present in the stored hydrocarbonaceous product and slowly separate therefrom. Minor amounts of aqueous liquids typically include between 0.01% and 25% aqueous liquid.

While high levels of biodegradability are ultimately desirable for hydrocarbonaceous products, rapid biodegradation during storage and transport is not desirable. Biodegradation during transport and storage and prior to use may cause many problems, as described previously.

According to the invention, certain hydrocarbonaceous products have been identified that are not only subject to biodegradation, but are also subject to rapid biodegradation. These "rapidly biodegradable hydrocarbonaceous products" may show visual growth of microorganisms in approximately ten days or less. The unusual speed of biodegradation of these specific hydrocarbonaceous products has not previously been recognized.

Products identified as rapidly biodegradable hydrocarbonaceous products according to the invention may include, for example, Fischer-Tropsch-derived liquid products and Low Aromatics Diesel Fuel. Preferably, the rapidly biodegradable hydrocarbonaceous products of the present invention are Fischer-Tropsch-derived liquid products, and more preferably, are Fischer-Tropsch-derived liquid products having a branching index less than five, preferably less than four, more preferably less than three.

It has now been determined that commercial use of Fischer-Tropsch hydrocarbonaceous products and other rapidly biodegradable hydrocarbonaceous products creates an increased need for control of biological degradation. In conventional hydrocarbonaceous products, various compounds, such as aromatics, and heteroatoms, such as sulfur, nitrogen, and the like, are present. These compounds and heteroatoms tend to be natural biocides or microbial inhibitors, and thus may naturally inhibit the growth of the microbes in conventional hydrocarbonaceous products. Therefore, when using conventional hydrocarbonaceous products, the products may be shipped and stored for a period of time without significant biodegradation. However, when using hydrocarbonaceous products identified as rapidly biodegradable, it has been determined that special measures must be taken to avoid problems resulting from rapid biodegradation during shipment and storage of these products to prevent biological degradation and microbial growth.

A product may be identified as rapidly biodegradable if visual growth of microorganisms occurs in the product in approximately ten days or less. Visual growth or formation of microorganisms may be measured quantitatively by measuring turbidity of the product in question. Turbidity is generally measured by using a turbidity meter, for example, a Hach Co. Model 2100 P Turbidimeter. A turbidity meter is a nephelometer that consists of a light source that illuminates a water/oil sample and a photoelectric cell that measures the intensity of light scattered at a 90° angle by the particles in the sample. A transmitted light detector also receives light that passes through the sample. The signal output (units in nephelometric turbidity units or NTUs) of the turbidimeter is a ratio of the two detectors. Meters can measure turbidity over a wide range from 0 to 1000 NTUs. The instrument must meet US-EPA design criteria as specified in US-EPA method 180.1.

By way of example, typical lube base oils measured at 75° F. have ranges of from 0 to 20 NTUs. Commercial Poly Alpha Olefins (PAOs) tend to have NTUs between 0 and 1. The visual formation of microorganisms is said to occur when the NTU value increases by two units from measurements made before and after microorganisms or inoculant are introduced into the sample. Measurements are made on the aqueous phase in contact with the hydrocarbon. Therefore, the NTU value of the rapidly biodegradable hydrocarbonaceous products of the present invention may show an increase of two or more units in approximately ten days or less after introduction of an inoculant.

The present invention relates to the use of deactivatable biocides in hydrocarbonaceous products, in particular, in rapidly biodegradable hydrocarbonaceous products. The use of traditional biocides in hydrocarbonaceous products causes disposal and wastewater problems. Due to a biocide's potential for continuing antimicrobial effects, water that contains biocides should not be discharged directly into the environment. Upon direct release into the environment, the biocide may kill or inhibit the growth of indigenous, and potentially desirable, bacterial, molds, fungi, and higher life forms. Therefore, the biocides may contaminate or pollute water supplies or require costly water treatment measures before disposal.

Further, the biocide may complicate necessary treatment of bilge water to remove residual hydrocarbons. For example, upon unloading of the hydrocarbonaceous products, the water that contacted the product may be contaminated with residual hydrocarbons. Therefore, this bilge water must be treated in on-shore facilities to remove hydrocarbons. For example, the water may be treated in a biological oxidation facility to remove residual hydrocarbons. Biocides present in the bilge water may make this treatment even more difficult and expensive. In addition, when the hydrocarbonaceous product is used for its intended purpose, residual biocide in the product may be introduced into the environment.

To avoid these environmental and treatment concerns, the biocides of the present invention are ones that are irreversibly deactivated once danger of microbial growth has ended (a "deactivatable biocide"). Thus, the biocide and/or the water containing the biocide may be removed and directly released or recycled without danger of environmental problems, or the water may be treated in an on-shore facility, for example, a biological oxidation facility, to remove residual hydrocarbons without added expense or complications due to the biocide. Further, the hydrocarbonaceous product may be used without contamination from residual biocide.

The deactivatable biocides of the invention may be advantageously used with conventional hydrocarbonaceous products and rapidly biodegradable hydrocarbonaceous products, including Fischer Tropsch derived liquid products.

In addition, the deactivatable biocides of the present invention may be advantageously used in any system that utilizes cooling water and/or other waste water streams. The deactivatable biocides of the invention may be added in an amount effective to prevent visible growth of microorganisms for at least 10 days under ambient conditions when exposed to a certified inoculant.

When the period during which microbial growth is expected or is to be prevented has ended, the deactivatable biocide of the present invention is deactivated before the hydrocarbonaceous product is used, or before the water which contacted the hydrocarbonaceous product (and incorporates the biocide) is released into the environment. In any system utilizing cooling water and/or other waste water streams, the deactivatable biocide of the present invention is deactivated before the water containing the biocide is released into the environment or recycled. Deactivation of the biocide minimizes environmental damage when the product, or streams that come in contact with the product, are introduced into the environment. Deactivation, according the present invention, is an irreversible process, i.e., the process may not be reversed re-generating the active biocide.

According to the present invention, the biocides are deactivatable biocides to avoid environmental and treatment concerns. Deactivatable biocides of the invention include aldehydes, alkynes, and the like. Deactivatable biocides of the invention that are aldehydes include, for example, glutaraldehyde, and deactivatable biocides of the invention that are alkynes, include, for example, 1-hexyne and propargyl alcohol.

By way of example, aldehydes are a preferred deactivatable biocide of the invention. While not being limited by theory, it is believed that aldehydes, including, for example, glutaraldehyde, act to inhibit growth of microorganisms by a mechanism similar to the Mannich reaction. By this mechanism, aldehydes, including, for example, glutaraldehyde, form complexes with non-hindered amines. These non-hindered amines include primary amines, ammonia, ammonium ions, or combinations thereof. In biological systems, these non-hindered amines may be amino acids. Cell walls of living organisms contain amino acids (non-hindered amines) that may provide a reactive site for aldehydes to react. Aldehydes may form cross-linking complexes with the amino acids on the cell surface, disrupting cellular function and killing the cells.

In particular, glutaraldehyde may be a preferred deactivatable biocide. Glutaraldehyde has rapid efficacy against a broad spectrum of microorganisms. Furthermore, glutaraldehyde is relatively insensitive to sulfide and is effective in controlling the growth of sulfate-reducing bacteria. Glutaraldehyde is nonionic and organic; thus, it is compatible with hydrocarbonaceous products. Glutaraldehyde also tolerates salts and hard water conditions. A further advantage of glutaraldehyde is that it may be irreversibly deactivated.

By way of examples, alkynes (compounds with carbon-carbon triple bonds, C≡C) are another preferred deactivatable biocide of the invention. While not being limited by theory, it is believed that alkynes may act to irreversibly inhibit alkane oxidizing enzymes, including, for example, mono-oxygenase enzymes. Alkane oxidizing enzymes are responsible for the key reactions that initiate degradation of paraffins or alkanes. Without alkane mono-oxygenase activity, microorganisms cannot degrade paraffins. Primary alkynes have been shown to irreversibly inhibit alkane oxidizing enzymes, while secondary alkynes, R—C/C—R, may be more effective on aromatic mono-oxygenases.

Alkynes may behave as "suicide substrates," and as such, activity of the oxidizing enzymes initiates the alkynes' inhibitory processes. The enzymes attempt to act on the alkynes, and this action causes irreversible binding of the alkynes to the active site of the enzyme. Binding of alkynes to the enzyme's active site inhibits the enzymes from causing further oxidation. It is important that the structure of the alkyne be similar to the structure of the alkane substrate, and the more similarity between the two, the more effective the inhibitory process is. As specific enzyme inhibitors, alkynes may be very effective biocides and at the same, time exhibit low general toxicity.

Alkynes may be especially effective biocides in Fischer-Tropsch-derived products due to the high concentration of paraffins or alkanes in Fischer-Tropsch products. Since primary alkynes have been shown to irreversibly inhibit alkane oxidizing enzymes, primary alkynes are preferred for use with Fischer-Tropsch-derived products. Preferably these primary alkynes (C≡C—R) have approximately the same average chain length as the average chain length of the alkanes in the Fischer-Tropsch-derived products.

Additional benefits of using alkynes as biocides in the present invention include their low inherent toxicity and their compatibility with hydrocarbonaceous products, including Fischer-Tropsch products.

By way of example, the alkynes used as biocides of the present invention may include, but are not limited to, 1-hexyne (HC≡C—$C_4H_9$), propargyl alcohol (HC≡C—$CH_2OH$), and the like.

The deactivatable biocides of the invention, including aldehydes and alkynes, are organic biocides. As organic biocides, they contain hydrogen, carbon, and oxygen and do not contain any significant degree of heteroatoms. In organic biocides, sulfur, nitrogen, halogens, and metals are only present as trace impurities. Therefore, the deactivatable biocides of the invention do not add any undesirable components (for example, aromatics or heteroatoms) to the hydrocarbonaceous products in which they are used, especially the Fischer Tropsch derived liquid products. Furthermore, since they are organic, the deactivatable biocides of the invention are compatible and easily used with hydrocarbonaceous products.

According to the present invention, the deactivatable biocides may be irreversibly deactivated by (a) reacting the biocide with a neutralizing agent to provide an inert or deactivated form of the biocide; or (b) complexing the biocide with a neutralizing agent to form a less toxic compound. As one of skill in the art will understand, the specific details of deactivation will depend on the particular deactivatable biocide used. The compounds, added in (a) to react with the biocide or in (b) to complex the biocide, are herein known as "neutralizing agents." The neutralizing agent according to the invention may be a compound, a series of compounds, or reaction conditions. According to the invention, the neutralizing agent may refer to compound (s) added to the biocide to irreversibly deactivate it or may refer to reaction conditions used to irreversibly deactivate the biocide. The neutralizing agents of the invention effectively and irreversibly deactivate the biocide. Deactivating the biocide means that the biocide no longer exhibits any significant degree of antimicrobial effects. Thus, the biocide may be released into the environment without affecting the growth of microorganisms or higher life forms. Furthermore, deactivation of the biocide is an irreversible process, i.e. the process may not be reversed re-generating the active biocide after it has been released into the environment.

By way of example, a deactivatable biocide of the present invention may be deactivated by reacting it with a neutralizing agent to provide an inert form. These reactions include, for example, oxidation and reduction. Oxidation can be accomplished by, for example, hydrogen peroxide, other organic peroxides, or an oxygenated halogen (for example, bleaches such as NaClO or $Ca(ClO)_2$). Oxidation is an effective means to deactivate virtually any type of biocide. In addition, oxidation can be performed in either the hydrocarbonaceous product or any water that has come in contact with the product. Although oxidation may be an effective, convenient means of deactivating the biocide, all oxidants may not be selective for the biocide and may thus react with other species in the product. Further, use of halogenated oxidants may create the risk of introducing halogens into the product.

As one of skill in the art would understand, biocides and subsequent oxidants may be used in the present invention; however, it is important to choose the biocide and subsequent oxidant carefully in view of the hydrocarbonaceous product. The oxidant should be selected such that it does not oxidize components of the hydrocarbonaceous product. As one of skill in the art would recognize, it may be possible to add an oxidant as a neutralizing agent to the water phase after separation of the hydrocarbonaceous product, thereby reducing the danger of oxidizing components of the hydrocarbonaceous product.

According to the invention, hydrogenation may also be an effective way to deactivate a biocide. The biocide may be hydrogenated while in contact with the hydrocarbonaceous product or may be hydrogenated after the water phase has been separated from the hydrocarbonaceous product. The process of hydrogenation is well known to those of skill in the art. Hydrogenation is performed using hydrogen gas. Typical catalysts for hydrogenation contain a Group VIII metal, such as platinum and palladium.

Complexing a biocide with a neutralizing agent may be used to form a less toxic compound and thus deactivate the biocide. When successful, the neutralizing agent is irreversibly complexed to the biocide to provide a compound that may be safely released into the environment. In determining neutralizing agents to complex with deactivatable biocides of the invention, the chemistry of the biocide's action to inhibit growth may be important.

By way of example, alkyne biocides may be effectively deactivated by hydrogenation. As a further example, aldehyde biocides, including, for example, glutaraldehyde, may be deactivated by irreversibly complexing or reacting them with nitrogen-containing compounds and oxygen scavengers. The nitrogen-containing compounds include, but are not limited to, primary amines, secondary amines, ammonia, amino alcohols, mixtures thereof, and the like. For example, glutaraldehyde may be deactivated by nitrogen-containing compounds including, for example, monoethanolamine, diethanolamine, methyldiethanolamine, diethylamine, aniline, and the like, and mixtures thereof.

An effective amount of neutralizing agent of the present invention is the amount that effectively deactivates or neutralizes the biocide rendering it virtually harmless to the environment and rendering it ineffectual to inhibit microbial growth. When an effective amount of neutralizing agent is used, the water containing the deactivated biocide may be safely released into the environment or processed in an on-shore facility. An effective amount of neutralizing agent to biocide is approximately 1 mole of neutralizing agent per mole of biocide. If excess neutralizing agent is used, the neutralizing agent may act as a biocide because it may be somewhat toxic. If much less neutralizing agent is added, it may not effectively deactivate or neutralize the biocide.

As one of skill in the art would readily understand and be able to devise, deactivation of the biocide may be accomplished in a variety of ways. By way of example, the neutralizing agent may be added to the storage or shipping device that contains the hydrocarbonaceous product. In addition, the neutralizing agent may be added to a biocide-containing aqueous phase in contact with the hydrocarbonaceous product, and then the aqueous phase and the hydrocarbonaceous product may be separated. Further, the biocide-containing aqueous phase and the hydrocarbonaceous product may be separated, and then the neutralizing agent may be added to the aqueous phase. As one of skill in the art would understand, a method to accomplish deactivation may be selecting in view of the neutralizing agent, the biocide, and the hydrocarbonaceous product.

The preferred hydrocarbonaceous products of the present invention are Fischer-Tropsch derived liquid products. An advantage of using Fischer Tropsch derived liquid products is that they do not contain nitrogen and sulfur and generally do not contain aromatic compounds. Accordingly, they have minimal health and environmental impact. These Fischer-Tropsch-derived fuels are considered "green fuels" and are desirable as environmentally friendly.

Catalysts and conditions for performing Fischer-Tropsch synthesis are well known to those of skill in the art, and are described, for example, in EP 0 921 184 A1, the contents of which are hereby incorporated by reference in their entirety. In the Fischer-Tropsch synthesis process, synthesis gas (syngas) is converted to liquid hydrocarbons by contact with a Fischer-Tropsch catalyst under reactive conditions. Typically, methane and optionally heavier hydrocarbons (ethane and heavier) can be sent through a conventional syngas generator to provide synthesis gas. Generally, synthesis gas contains hydrogen and carbon monoxide, and may include minor amounts of carbon dioxide and/or water. The presence of sulfur, nitrogen, halogen, selenium, phosphorus and arsenic contaminants in the syngas is undesirable. For this reason, and depending on the quality of the syngas, it is preferred to remove sulfur and other contaminants from the feed before performing the Fischer Tropsch chemistry. Means for removing these contaminants are well known to those of skill in the art. For example, ZnO guardbeds are preferred for removing sulfur impurities. Means for removing other contaminants are well known to those of skill in the art. It also may be desirable to purify the syngas prior to the Fischer Tropsch reactor to remove carbon dioxide produced during the syngas reaction and any additional sulfur compounds not already removed. This can be accomplished, for example, by contacting the syngas with a mildly alkaline solution (e.g., aqueous potassium carbonate) in a packed column.

In the Fischer Tropsch process, liquid and gaseous hydrocarbons are formed by contacting a synthesis gas comprising a mixture of $H_2$ and CO with a Fischer Tropsch catalyst under suitable temperature and pressure reactive conditions. The Fischer Tropsch reaction is typically conducted at temperatures of about 300 to 700° F. (149 to 371° C.), preferably about from 400 to 550° F. (204 to 228° C.); pressures of about from 10 to 600 psia, (0.7 to 41 bars), preferably 30 to 300 psia, (2 to 21 bars) and catalyst space velocities of from about 100 to about 10,000 cc/g/hr., preferably 300 to 3,000 cc/g/hr.

Examples of conditions for performing Fischer-Tropsch type reactions are well known to those of skill in the art. Suitable conditions are described, for example, in U.S. Pat. Nos. 4,704,487, 4,507,517, 4,599,474, 4,704,493, 4,709,108, 4,734,537, 4,814,533, 4,814,534 and 4,814,538, the contents of each of which are hereby incorporated by reference in their entirety.

The products of the Fischer Tropsch synthesis process may range from $C_1$ to $C_{200+}$ with a majority in the $C_5$ to $C_{100+}$ range, and the products may be distributed in one or more product fractions. The reaction can be conducted in a variety of reactor types, for example, fixed bed reactors containing one or more catalyst beds, slurry reactors, fluidized bed reactors, or a combination of different type reactors. Such reaction processes and reactors are well known and documented in the literature. In the Fischer Tropsch process, the desired Fischer Tropsch product typically will be isolated by distillation.

Slurry Fischer-Tropsch processes, which is a preferred process in the practice of the invention, utilize superior heat (and mass) transfer characteristics for the strongly exothermic synthesis reaction and are able to produce relatively high molecular weight, paraffinic hydrocarbons when using a cobalt catalyst. In a slurry process, a syngas comprising a mixture of $H_2$ and CO is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions. The mole ratio of the hydrogen to the carbon monoxide may broadly range from about 0.5 to 4, but is more typically within the range of from about 0.7 to 2.75 and preferably from about 0.7 to 2.5. A particularly preferred Fischer-Tropsch process is taught in EP 0609079, herein incorporated by reference in its entirety.

The products from Fischer-Tropsch reactions performed in slurry bed reactors generally include a light reaction product and a waxy reaction product. The light reaction product (i.e. the condensate fraction) includes hydrocarbons boiling below about 700° F. (e.g., tail gases through middle distillates), largely in the $C_5$–$C_{20}$ range, with decreasing amounts up to about $C_{30}$. The waxy reaction product (i.e., the wax fraction) includes hydrocarbons boiling above 600° F. (e.g., vacuum gas oil through heavy paraffins), largely in the $C_{20}$+ range, with decreasing amounts down to $C_{10}$. Both the light reaction product and the waxy product are substantially paraffinic. The products generally comprise greater than 70% normal paraffins, and often greater than 80% normal paraffins. The light reaction product comprises paraffinic products with a significant proportion of alcohols and olefins. In some cases, the light reaction product may comprise as much as 50%, and even higher, alcohols and olefins.

The product from the Fischer-Tropsch process may be further processed using, for example, hydrocracking, hydroisomerization, and hydrotreating. Such processes crack the larger synthesized molecules into fuel range and lube range molecules with more desirable boiling points, pour points, and viscosity index properties. Such processes may also saturate oxygenates and olefins to meet the particular needs of a refinery. These processes are well known in the art and do not require further description here.

In general, suitable Fischer-Tropsch catalysts comprise one or more Group VIII catalytic metals such as Fe, Ni, Co, Ru and Re. Additionally, a suitable catalyst may contain a promoter. Thus, a preferred Fischer-Tropsch catalyst comprises effective amounts of cobalt and one or more of Re, Ru, Pt, Fe, Ni, Th, Zr, Hf, U, Mg and La on a suitable inorganic support material, preferably one which comprises one or more refractory metal oxides. In general, the amount of cobalt present in the catalyst is between about 1 and about 50 weight percent of the total catalyst composition. The catalysts can also contain basic oxide promoters such as $ThO_2$, $La_2O_3$, MgO, and $TiO_2$, promoters such as $ZrO_2$, noble metals (Pt, Pd, Ru, Rh, Os, Ir), coinage metals (Cu, Ag, Au), and other transition metals such as Fe, Mn, Ni, and Re. Support materials including alumina, silica, magnesia and titania or mixtures thereof may be used. Preferred supports for cobalt containing catalysts comprise titania. Useful catalysts and their preparation are known to those of skill in the art.

Certain catalysts are known to provide chain growth probabilities that are relatively low to moderate, for example, iron-containing catalysts, and the reaction products include a relatively high proportion of low molecular ($C_{2-8}$) weight olefins and a relatively low proportion of high molecular weight ($C_{30}+$) waxes. Certain other catalysts are known to provide relatively high chain growth probabilities, for example, cobalt-containing catalysts, and the reaction products include a relatively low proportion of low molecular ($C_{2-8}$) weight olefins and a relatively high proportion of high molecular weight ($C_{30}+$) waxes. Such catalysts are well known to those of skill in the art and can be readily obtained and/or prepared.

A preferred Fischer-Tropsch product of the present invention has a branching index of less than five, preferably less than four, more preferably less than three. Fischer-Tropsch (FT) derived products include, for example, Fischer-Tropsch naphtha, Fischer-Tropsch jet fuel, Fischer-Tropsch diesel fuel, Fischer-Tropsch solvent, Fischer-Tropsch lube base stock, Fischer-Tropsch lube base oil, Fischer-Tropsch lube base stock feedstock, and mixtures thereof.

Distillate fuels, derived from the Fischer-Tropsch process, have excellent burning properties. Fischer-Tropsch products contain essentially no aromatics or heteroatoms, such as sulfur and nitrogen. In addition, Fischer-Tropsch distillate fuels are highly paraffinic; paraffins are the majority components (>50%) and can exceed 70% and even 95%. As a class, paraffins are the most biodegradable compounds found in petroleum and are preferentially metabolized by microbes. Alkane oxygenases are the enzymes that initiate paraffin (i.e. alkane) degradation. In contrast to Fischer-Tropsch products, conventional hydrocarbonaceous products contain many components, with paraffins being only a minority component.

Since Fischer-Tropsch products contain essentially no natural biocides (i.e., aromatics nitrogen, sulfur) and contain paraffins as a majority component, Fischer-Tropsch products are biodegradable. According to the present invention, it has been determined that Fischer-Tropsch products are rapidly biodegradable, and therefore, are more susceptible to biodegradation during normal transport and storage than comparable petroleum fractions. The greater susceptibility for biodegradation of Fischer-Tropsch products increases the need for effective biocides during shipment and storage of these products.

A Fischer-Tropsch-derived liquid product may be recovered directly from a Fischer-Tropsch reaction zone, or alternatively, from a distillate and/or a bottoms fraction from the distillation of a Fischer-Tropsch reaction zone product and/or alternatively from a hydroprocessed or cracked stream which originated, at least in part, from a Fischer-Tropsch syntheses process. Hydroprocessing includes hydrotreating, hydroisomerization and hydrocracking. Such processes crack the larger synthesized molecules into fuel range molecules with more desirable boiling points, pour points, and viscosity index properties. Such processes may also saturate oxygenates and olefins to meet the particular needs of a refinery. These processes are well known to those of skill in the art. For example, hydroprocessing conditions and catalysts, are taught in co-pending U.S. patent application Ser. No. 09/854195, filed May 11, 2001, and entitled "Co-Hydroprocessing of Fischer-Tropsch Products and Natural Gas Well Condensate," the entire disclosure of which is incorporated herein by reference for all purposes.

The present invention provides processes that utilize the various products obtained or obtainable from a Fischer Tropsch reaction. The processes described herein provide Fischer Tropsch fractions that can be processed to provide Fischer Tropsch derived liquid products. The Fischer Tropsch derived liquid products are highly paraffinic and have a low sulfur content. The highly paraffinic Fischer Tropsch derived liquid products of the invention may be prepared by any of the means known to those in the art. Preferably, the highly paraffinic Fischer Tropsch derived liquid products of the invention may be prepared from Fischer Tropsch products by processes that include hydrocracking, hydroisomerization, oligomerization, isomerization, hydrotreating, hydrogenation, or combinations of these processes.

The processes described herein also provide products that may be isolated and used directly as deactivatable biocides and products that may be isolated and converted into deactivatable biocides by chemical processes well know to those of skill in the art, including for example, oxidation, dehydration, and/or dehydrogenation. The Fischer Tropsch products, which may be used as deactivatable biocides, include substances that inhibit alkane degradation and thus prevent microbial decomposition of Fischer-Tropsch products and minimize bacterial growth. These products are herein identified as "Fischer Tropsch derived deactivatable biocides." Fischer Tropsch products that may be used to provide Fischer Tropsch derived deactivatable biocides include, for example, oxygenates (including alcohols, aldehydes, and carboxylic acids), olefins, alkynes, and mixtures thereof.

Olefins and oxygenates may be derived from light Fischer Tropsch products. In addition, olefins may be formed, for example, by a thermal cracking process performed on heavy Fischer Tropsch products. Furthermore, oxygenates may be generated as a component of the waste-water generated as part of the Fischer-Tropsch process.

By way of example, the olefins and oxygenates derived from a Fischer Tropsch process may be used to provide aldehydes and alkynes by chemical processes which include oxidation and/or dehydrogenation. One of skill in the art would readily be able to devise methods to generate and isolate olefins and oxygenates from a Fischer-Tropsch process and convert these olefins and oxygenates to aldehydes and alkynes. Alternatively, waste-water generated in the Fischer-Tropsch process may contain a variety of oxygenated hydrocarbons. These oxygenated hydrocarbons may also be used as directly or used to generate aldehydes.

Accordingly, a Fischer Tropsch process may be used to generate Fischer Tropsch derived liquid products and Fischer Tropsch derived deactivatable biocides. The deactivatable biocides used with Fischer Tropsch derived products preferably are ones derived from the Fischer Tropsch process. Deriving the deactivatable biocide from the Fischer Tropsch process serves several benefits. It removes olefins and oxygenates from the Fischer Tropsch feedstock reducing the amount of potential catalyst poisons in the stream. It also provides a method of converting Fischer Tropsch products into biocides increasing the overall efficiency of the Fischer Tropsch process. Furthermore, Fischer-Tropsch-derived biocides do not have to be purchased from a third party, do not have to be generated at a remote location, and do not have to be shipped from a remote location to the Fischer Tropsch process site.

Fischer-Tropsch-derived deactivatable biocides are well suited for use with Fischer Tropsch products. For example, Fischer Tropsch derived biocides do not contain undesirable heteroatoms, such as sulfur, nitrogen, and metals. Fischer Tropsch derived biocides are compatible for use with Fischer Tropsch products. Fischer Tropsch derived biocides do not increase the tendency of Fischer-Tropsch products to oxidize. Furthermore, Fischer Tropsch derived are produced as part of the Fischer-Tropsch process.

According to the present invention, the deactivatable biocide and the hydrocarbonaceous product may be mixed in a variety of ways to inhibit growth and reproduction of microorganisms in the hydrocarbonaceous product. By way of example, the deactivatable biocide and the hydrocarbonaceous product may be mixed and then pumped into the storage or transportation device. In addition, the deactivatable biocide may be added to an empty storage or transportation device and then the hydrocarbonaceous product may be added. Further, the hydrocarbonaceous product may be pumped into a storage or transportation device and then the deactivatable biocide may be added to either the hydrocarbonaceous product or to an aqueous phase that is in contact or will be in contact with the hydrocarbonaceous product. As another example, the deactivatable biocide may be added to an aqueous phase in the storage or transportation device and then the hydrocarbonaceous product may be added. Further, the storage or transportation device may be coated with the deactivatable biocide before the hydrocarbonaceous product is added and any aqueous phase accumulates. This coating may occur as part of the manufacturing of the storage or transportation device or as preparation for each use of the device.

An effective amount of a deactivatable biocide of the present invention is the amount that inhibits microbial growth in the hydrocarbonaceous product for approximately 10 days. The effective amount may vary depending on both the hydrocarbonaceous product and the biocide, but is generally added in a concentration of less than about 1 wt %. Preferably, the deactivatable biocide may be added at a concentration of less than 1000 ppm, more preferably less than 100 ppm, and most preferably less than about 25 ppm.

The present invention also relates to methods of inhibiting the growth and reproduction of microorganisms in hydrocarbonaceous products, including both conventional hydrocarbonaceous products and rapidly biodegradable hydrocarbonaceous products, containing minor amounts of aqueous liquids.

In one method, an effective amount of a deactivatable biocide is added to a hydrocarbonaceous product to resist visible growth of microorganisms for at least 10 days under ambient conditions when exposed to a certified inoculant. Resisting visible growth for at least 10 days means that the visual formation of microorganisms does not occur for at least 10 days. As explained previously, visual growth of microorganisms is said to occur when the NTU value increases by two units from measurements made before and after the inoculant introduced into the sample. Therefore, resisting visual growth for at least 10 days means that the NTU value does not increase by two units. A certified inoculant consists of a source of bacteria initially isolated at ambient conditions using a rapidly biodegradable hydrocarbonaceous product as the sole source of carbon and energy, and that has been shown to grow on the hydrocarbonaceous product through two or more successive inoculations. Ambient conditions mean a temperature between 10 and 40° C. and a pH between 6 and 8.5.

In this method, an effective amount of a neutralizing agent is added to deactivate the biocide after the period in which growth and reproduction of microorganisms is expected. This method may also comprise the step of separating the aqueous phase from the hydrocarbonaceous product. Deactivation of the biocide minimizes environmental damage when the product, or streams that come in contact with the product, are introduced into the environment. Deactivation of the biocide may be accomplished by, for example, deactivation or neutralization of the biocide in the aqueous phase while the hydrocarbonaceous product is in contact with the aqueous phase or by deactivation or neutralization of the biocide in the aqueous phase after separation of the aqueous phase from the hydrocarbonaceous product. After separation of the aqueous phase, the method may also comprise treating the aqueous phase in an on-shore treatment facility, for example a biological oxidation facility, to remove any residual hydrocarbons from the aqueous phase.

The present invention preferably relates to a method of inhibiting the growth and reproduction of microorganisms in a Fischer-Tropsch-derived liquid product containing minor amounts of aqueous liquids. Preferably the Fischer-Tropsch-derived liquid product has a branching index of less than five, more preferably less than four, and most preferably less than three. In this method a Fischer-Tropsch derived liquid product is synthesized by a Fischer Tropsch process. The product recovered from a Fischer-Tropsch process may range from $C_5$ to $C_{20}$+ and may be distributed in one or more product fractions. In the Fischer Tropsch process, the desired Fischer Tropsch product typically will be isolated by distillation.

The products from Fischer-Tropsch reactions performed in slurry bed reactors generally include a light reaction product and a waxy reaction product. The light reaction product (i.e. the condensate fraction) includes hydrocarbons boiling below about 700° F. (e.g., tail gases through middle distillates), largely in the $C_5$–$C_{20}$ range, with decreasing amounts up to about $C_{30}$. The waxy reaction product (i.e. the wax fraction) includes hydrocarbons boiling above 600° F. (e.g., vacuum gas oil through heavy paraffins), largely in the $C_{20}$+ range, with decreasing amounts down to $C_{10}$. Both the light reaction product and the waxy product are substantially paraffinic. The waxy product generally comprises greater than 70% normal paraffins, and often greater than 80% normal paraffins. The light reaction product comprises paraffinic products with a significant proportion of alcohols and olefins. In some cases, the light reaction product may comprise as much as 50%, and even higher, alcohols and olefins.

The product from the Fischer-Tropsch process may be further processed using, for example, hydrocracking, hydroisomerization, hydrotreating. Such processes crack the larger synthesized molecules into fuel range and lube range molecules with more desirable boiling points, pour points, and viscosity index properties. Such processes may also saturate oxygenates and olefins to meet the particular needs of a refiner. These processes are well known in the art and do not require further description here.

To the Fischer Tropsch product is added an effective amount of deactivatable biocide to provide a product that resists visible growth of microorganisms for at least 10 days under ambient conditions when exposed to a certified inoculant. The deactivatable biocide is preferably a Fischer-Tropsch-derived biocide. If the biocide is a Fischer-Tropschderived biocide, the Fischer Tropsch process may be used to provide both the biocide and the liquid product. An appropriate biocide may be isolated from the products of the Fischer Tropsch process directly, for example, by distillation or chromatographic separation. In the alternative, appropriate products may be isolated from the Fischer Tropsch process and chemical processes may be used to provide deactivatable biocides from these products. The appropriate products used to provide deactivatable biocides may include olefins and/or alcohols, and the chemical processes may include dehydration, dehydrogenation, and/or oxidation. It is preferred and efficient to use a Fischer-Tropsch-derived biocide with the Fischer-Tropsch-derived liquid because both may be made in the same synthesis process.

The method also includes the step of adding a neutralizing agent to deactivate the biocide after the period in which growth and reproduction of microorganisms is expected. The biocide is irreversibly deactivated, i.e., the biocide does not re-generate to become active upon release to the environment. The method may also comprise the step of separating the aqueous phase from the hydrocarbonaceous product. After separation of the aqueous phase, the method may also comprise treating the aqueous phase in a biological oxidation facility to remove any residual hydrocarbons from the aqueous phase.

EXAMPLES

The invention will be further explained by the following illustrative examples that are intended to be non-limiting.

Example 1

Preparation of Diesel Fuel Samples

A Fischer-Tropsch product was generated by reacting synthesis gas over an iron-containing catalyst. The product was separated into a diesel boiling range product (A) and a wax. The diesel product (A) was hydrotreated to remove oxygenates and olefins. The wax was hydrocracked over a sulfided catalyst consisting of amorphous silica-alumina, alumina, tungsten and nickel. A second diesel product (B) was recovered from the effluent of the hydrocracker. The two diesel products were blended in the proportion of 82% B and 18% A by weight. Properties of the Fischer-Tropsch (FT) diesel fuel blend are shown below in Table 1.

TABLE I

Properties of FT Diesel Fuel

| Tests | ASTM D975 Specifications | Fischer-Tropsch Diesel |
|---|---|---|
| Density, 15° C. | | 0.7695 |
| Sulfur, ppm | 0.05(% mass max.) | <6 |
| Nitrogen, ng/µl | | 0.69 |
| Cetane Index ASTM D976 | 40(min.) | 76 |
| Normal Paraffins, wt % | | 17.24 |
| Non Normal Paraffins, wt % | | 82.76 |
| Distillation D86, ° F. | | 333 |
| 10% | | 371 |
| 50% | | 478 |
| 90% | 540(min.), 640(max.) | 631 |
| 95% | | 653 |
| EP | | 670 |

Samples of conventional diesel fuel (C) and California Alternate Low Aromatics Diesel Fuel (ALAD) were also obtained. Properties of these two are shown below in Table II.

TABLE II

Properties of Commercial Diesel Fuels

| Diesel Type: | C | ALAD |
|---|---|---|
| Density @ 15° C., g/mL | 0.8551 | 0.8418 |
| Sulfur, ppm | 4190 | 24 |
| Nitrogen, ppm | 296 | <1 |
| Cetane Index (D 976) | 46.4 | 55.0 |
| D 86 Distillation, ° F. | | |
| Start | 348 | 366 |
| 5% | 385 | 448 |
| 10% | 404 | 479 |
| 30% | 470 | 535 |
| 50% | 520 | 566 |
| 70% | 568 | 593 |
| 90% | 634 | 632 |
| 95% | 661 | 652 |
| End Point | 685 | 671 |
| Recovery, % | 98.6 | 98.4 |

Both commercial diesel fuels contain significantly more aromatics than the Fischer-Tropsch diesel fuel, with sample C, the conventional diesel fuel, containing the most. The ALAD sample contains low levels of nitrogen and sulfur.

Example 2

Certification of the Inoculum for Determining the Speed of Biodegradation

Inoculum Development: The original alkane degrading culture was produced by growing microorganisms from a variety of sources including soils and water known to be contaminated with crude oil and petroleum products. A few micrograms of each source material were added to the minimal medium described below using FT diesel as the carbon source. After substantial growth was observed, organisms were removed from the suspension by pipette and added to fresh minimal medium containing FT diesel as the carbon source. This source of organisms was used for subsequent experiments. $n\text{-}C_{16}$ could also be used as a carbon source for developing the inoculum.

To determine if the inoculum and other factors of the test, such as growth medium, are suitable for use in determining the speed of biodegradation, $n\text{-}C_{16}$ was obtained from Aldrich Chemical company, and used as a standard hydrocarbon representative of rapidly biodegradable hydrocarbonaceous products.

Growth Media: A standard minimal media containing only inorganic nutrients required for bacterial growth was used. The medium used to supply inorganic micronutrients to the growing culture of alkane degrading organisms consisted of 0.1 g/L $MgSO_4 \cdot 7H_2O$, 0.5 g/L $NaNO_3$, 0.02 millimolar $FeSO_4$ and 0.63 g/L $K_2HPO_4$ and 0.19 g/L $KH_2PO_4$ to achieve a pH of 7 to 7.3.

Test Conditions: 90 ml of growth media and 10 ml of the product to be tested (n-C16) were added to 250 ml flasks. 100 µl of the bacterial inoculum was added to each flask. After inoculation, the flasks were place on a shaker-table (135 rpm) at room temperature in contact with air and observed daily.

The $n\text{-}C_{16}$ showed visual growth of microorganisms at three days in the water phase. Visual growth of microorganisms with $n\text{-}C_{16}$ under these test conditions at less then 4 days demonstrates that the inoculum is certified for determining the speed of biodegradation in this application, and that other factors in the experiment are suitable for this application.

The visual formation of microorganisms can also be measured quantitatively by measuring the turbidity. Turbidity is generally measured by using a turbidity meter, such as a Hach Co. Model 2100 P Turbidimeter. A turbidity meter is a nephelometer that consists of a light source that illuminates a water/oil sample and a photoelectric cell that measures the intensity of light scattered at a 90° angle by the particles in the sample. A transmitted light detector also receives light that passes through the sample. The signal output (units in nephelometric turbidity units or NTUs) of the turbidimeter is a ratio of the two detectors. Meters can measure turbidity over a wide range from 0 to 1000 NTUs. The instrument must meet US-EPA design criteria as specified in US-EPA method 180.1.

Typical lube base oils measured at 75° F. have ranges from 0–20 NTUs. Commercial polyalpholefins (PAOs) tend to have NTUs between 0–1.

When the appearance of the oils is examined (in simulation of a customer's opinion) the following relates to the value of the NTU and the appearance:

| NTU Value | Appearance |
| --- | --- |
| 20 | Cloudy |
| 2–5 | Possibly acceptable, but noticeable haze |
| 0.5–2 | Clear and bright |

References drinking water must be <1.0 recreational water must be <5.0

The visual formation of microorganisms is said to occur when the NTU value increases by two units from measurements made before the microorganisms were introduced into the sample.

Example 3

Test for Rapidly Biodegradable Hydrocarbonaceous Products

The following examples identify Rapidly Biodegradable Hydrocarbonaceous Products.

Test Conditions: 90 ml of growth media and 10 ml of the product to be tested were added to 250 ml flasks. 100 µl of the bacterial inoculum was added to each flask except for the sterile controls.

After inoculation, the flasks were place on a shaker-table (135 rpm) at room temperature in contact with air and observed daily. The sterile control showed no growth or discoloration.

The following Table III summarizes the appearance of visual growth in the three products tested: FT diesel fuel, ALAD Diesel, and conventional diesel.

TABLE III

| | Appearance of Visual Growth | | |
| --- | --- | --- | --- |
| Day | FT Diesel Fuel | ALAD Diesel | Conventional Diesel |
| 0 | − | − | − |
| 1 | − | − | − |
| 2 | − | − | − |
| 3 | + | + | − |
| 4 | + | + | − |
| 5 | + | + | − |
| 6 | + | + | − |
| 7 | + | + | − |
| 8 | + | + | − |

− No Growth
+ Growth (White Unless Otherwise Indicated)

Growth under ten days is representative of a product that is rapidly biodegradable because storage of products for ten days is common, and formation of a visible deposit is not acceptable. Both the FT and the ALAD samples were rapidly biodegradable under these standards while the conventional diesel fuel was not.

Example 4

Evaluation of Biocides

The ability of biocides to inhibit growth on a FT diesel and a low aromatics diesel fuel from sample 1 was investigated.

Test Conditions: 90 ml of growth media and 10 ml of either FT diesel or low sulfur (ALAD) diesel was added to 250 ml flasks. 10 µl of the bacterial inoculum was added to each flask except for the sterile controls. In addition to 2 alkynes, glutaraldehyde (glutaric dialdehyde 50%), was tested. The following summarizes the test conditions:

Sterile control (media boiled prior to adding FT or ALAD, not inoculated)

Inculated control (no inhibitor)

100 ppm inhibitor (on a total test volume basis or 1000 ppm in diesel)

1% inhibitor (on a total test volume basis or 10% in diesel).

Three inhibitors were evaluated:

G—glutaraldehyde (glutaric dialdehyde 50%)

H—1-hexyne

P—Propargyl alcohol

After inoculation, the flasks were place on a shaker-table (135 rpm) at room temperature and observed daily.

The following Table IV summarizes the test results obtained using Fischer-Tropsch diesel fuel.

TABLE IV

Test Results on Fischer-Tropsch Diesel Fuel

| Day | Sterile Control | No Biocide | FT Diesel + 100 ppm G | FT Diesel + 1 Wt % G | FT Diesel + 100 ppm P | FT Diesel + 1 Wt % P | FT Diesel + 100 ppm H | FT Diesel + 1 Wt % H |
|---|---|---|---|---|---|---|---|---|
| 0 | - | - | - | - | - | - | - | - |
| 1 | - | - | - | - | - | - | - | - |
| 5 | - | + | - | - | - | - | + | - |
| 7 | - | + | - | - | + | - | + | - |
| 8 | - | + | - | - | + | - | + | - |
| 19 | - | + | + | - | + | - | + | - |

− No Growth
+ Growth (White Unless Otherwise Indicated)

These results demonstrate that all three biocides were effective, with glutaraldehyde being effective at a lower concentration. An effective amount of a biocide is the amount that inhibits microbial growth in a rapidly biodegradable hydrocarbonaceous product for 10 days. As can be seen, these concentrations can vary from less than 100 ppm to about 1 wt %. A suitable range would be 25 ppm to 1 wt %, except where the biocide is a conventional petroleum hydrocarbonaceous product. In this case, the suitable range is between 10 and 90 wt %, preferably 25 to 75 wt %, most preferably about a 50—50 mixture.

The following Table V summarizes the test results obtained using ALAD diesel fuel.

TABLE V

Test Results on ALAD Diesel Fuel

| Day | LA Diesel Fuel | LA Diesel + 100 ppm G | LA Diesel + 1 Wt % G | LA Diesel + 100 ppm H | LA Diesel + 1 Wt % H | LA Diesel + 100 ppm P | LA Diesel + 1 Wt % P |
|---|---|---|---|---|---|---|---|
| 0 | - | - | - | - | - | - | - |
| 1 | - | - | - | - | - | - | - |
| 5 | + | - | - | + | - | + Yellow | - |
| 7 | + | - | - | + | - | + Yellow | - |
| 8 | + | - | - | + | - | + Yellow | - |
| 19 | + | - | - | + | - | + Yellow | - |

− No Growth
+ Growth (White Unless Otherwise Indicated)

These results show that all three biocides were effective, with glutaraldehyde being effective at a lower concentration.

Example 5

Test of Nutrients

The results in Example 4 suggested that the alkynes inhibited growth in FT diesel and in ALAD. A test was conducted to evaluate whether the inhibition was specific for substrates that required oxygenase activity or a general inhibitor of bacterial growth. In this test, growth on a microbial media containing easily degradable organics (sugar, yeast extract) was evaluated in the presence of FT with 1% of each of the inhibitors. 400 ml of media containing 1000 ppm microbial growth substrate was split between 4 flask. 10 ml FT was added to each flask. Three of the flasks received one of the inhibitors. They were inoculated with 100 µl from the FT inoculated control flask of experiment 3.

All three of the compounds showed inhibited growth on a rich media containing sugars and yeast extract. This suggests that the mode of inhibition is more general than merely inactivating mono-oxygenase enzymes.

Example 6

Partition of the Biocide

This example demonstrates that the majority of the biocides are partitioned in the water phase. Since the majority of the biocide remains mainly in the water phase, the water in contact with the hydrocarbonaceous product should be treated prior to disposal.

The rapidly biodegradable hydrocarbonaceous product was placed in contact with water that contained an effective level of biocide (e.g. 1 wt %). Subsequently, the rapidly biodegradable hydrocarbonaceous product was removed and replaced with a fresh sample of rapidly biodegradable hydrocarbonaceous product. Microbial growth was still inhibited (no growth after 16 days) showing that the biocide remained at an effective concentration in the water.

Example 7

Evaluation of Lower Amounts of Water

The above examples used higher amounts of water than might typically be expected during transportation and storage of a rapidly biodegradable hydrocarbonaceous product. A higher amount of water was used to make clear observations in the above experiments.

In this example, an experiment was done using a lower amount of water. 90% Fischer-Tropsch diesel fuel was mixed with 10% minimal media. One flask was used as a control and the other contained 100 ppm hexyne. The control flask showed growth in 5 days, while the hexyne inhibited flask showed no growth after 16 days.

Example 8

Equivalence of n-$C_{16}$ and Fischer-Tropsch Diesel Fuel as Rapidly Biodegradable Hydrocarbonaceous Products To demonstrate the equivalence of n-$C_{16}$ and the Fischer-Tropsch diesel fuel, 90 ml of media and 10 ml of either FT diesel or n-$C_{16}$ were added to 250 ml flasks. 10 µl of the bacterial inoculum was added to each flask. Both showed no growth at 2 days, but 6 days (the next observation), both showed growth. The onset of growth in both materials at approximately the same time indicates that they have a nearly equivalent onset of microbial growth. Therefore, both can be used interchangeably as rapidly biodegradable hydrocarbonaceous products.

Comparative Example 9

Neutralization of Biocides—$H_2O_2$ and $NH_4Cl$

This example demonstrates that $H_2O_2$ and $NH_4Cl$ are not effective in neutralizing biocides. In this experiment, minimal medium, containing 1, 10 or 100 ppm of glutaraldehyde, were mixed with a five times molar excess of $H_2O_2$ or $NH_4Cl$. Hydrocarbonaceous product and bacteria were then added to the mixture. While microbial growth was observed after 5 days in control samples containing no glutaraldehyde, no growth was observed after 14 days in samples containing glutaraldehyde and $H_2O_2$ or $NH_4Cl$. This growth demonstrates that these species were ineffective in neutralizing the glutaraldehyde. Presumably, the $H_2O_2$ remained toxic, and the $NH_4Cl$ did not form a complex with the glutaraldehyde.

Example 10

Neutralization of Biocides with Monoethanolamine

This example demonstrates that amines and aminoalcohols can be used to neutralize biocides. The optimum amount of neutralizing agent to biocide is approximately 1 mole per mole. If excess neutralizing agent is added, it too can act as a biocide because it is toxic, although much less so than the biocide itself. If a large amount of biocide is added (100 ppm or more of glutaraldehyde), the amount of amine added should be fairly close to a 1:1 molar ratio to avoid toxicity problems from the neutralizing amine.

In all experiments a 10:1 ratio of minimal media to Fischer-Tropsch diesel fuel were prepared and evaluated in 250 ml flasks. To the flasks, various levels of glutaraldehyde (G) and monoethanolamine (MEA) were added.

|           | 5X MEA | 2X MEA | 1X MEA | no MEA |
|-----------|--------|--------|--------|--------|
| 100 ppm G | X      | X      | X      | X      |
| 10 ppm G  | X      | X      | X      | X      |
| 1 ppm G   | X      | X      | X      | X      |

Then 10 μl of the bacterial inoculum was added to each flask.

In addition to these experiments, several controls were run without Gluteraldehyde as follows:

1 ppm MEA control
10 ppm MEA control
100 ppm MEA control
500 ppm MEA control
no G/no MEA control The results of these experiments are shown in Table VI.

TABLE VI

Neutralization of Biocides with MEA.

| Time days) | 0 | 1 | 2 | 3 | 7 | 9 | 14 |
|---|---|---|---|---|---|---|---|
| 100 ppm G + 5X MEA | − | − | − | − | − | − | − |
| + 2X MEA | − | − | − | − | − | − | − |
| + 1X MEA | − | − | − | − | + | + | + |
| No MEA | − | − | − | − | − | − | − |

TABLE VI-continued

Neutralization of Biocides with MEA.

| Time days) | 0 | 1 | 2 | 3 | 7 | 9 | 14 |
|---|---|---|---|---|---|---|---|
| 10 ppm G + 5X MEA | − | − | − | − | + | + | + |
| + 2X MEA | − | − | − | + | + | + | + |
| + 1X MEA | − | − | − | − | + | + | + |
| no MEA | − | − | − | − | − | − | − |
| 1 ppm G + 5X MEA | − | − | − | − | + | + | + |
| + 2X MEA | − | − | − | + | + | + | + |
| + 1X MEA | − | − | − | − | + | + | + |
| no MEA | − | − | − | − | − | + | + |
| Controls: | | | | | | | |
| 1 ppm MEA | − | − | − | + | + | + | + |
| Time days) | 0 | 1 | 2 | 3 | 7 | 9 | 14 |
| 10 ppm MEA | − | − | − | + | + | + | + |
| 100 ppm MEA | − | − | − | − | − | − | + |
| 500 ppm MEA | − | − | − | − | − | − | + |
| no G/no MEA | − | − | − | + | + | + | + |

The control results without MEA and without gluteraldehyde shows growth in 3 days as expected. Low levels of MEA in the controls (less than 100 ppm) are not significantly toxic and do not delay the onset of microbial growth. High levels of MEA in the control (100 ppm and higher) are toxic and do delay the onset of microbial growth.

In general, the results demonstrate that adding an equal molar amount of MEA to gluteraldehyde is effective in neutralizing the gluteraldehyde and permitting microbial growth. This is an indication that the biocide has been neutralized, and the water containing the neutralized biocide could safely be discharged or processed in on-shore facilities.

The results also show that 1 ppm of gluteraldehyde is moderately effective in delaying the onset of microbial growth—delayed from 3 days to 9 days. 10 ppm is more effective—delayed from 3 days to more than 14 days.

At low levels of gluteraldehyde (below 100 ppm), less than 5 moles MEA to gluteraldehyde are needed to be effective in neutralizing the gluteraldehyde and to yield a water fraction that permits microbial growth, and so by inference is safe to discharge or treat in on-shore facilities. The minimum ratio of MEA to gluteraldehyde is below 1.0 and may be as low as 0.2.

At high levels of gluteraldehyde (100 ppm and above), a precise amount of MEA, approximately equal to 1 mole of MEA to gluteraldehyde, is needed to yield a water fraction that permits microbial growth, and so by inference is safe to discharge or treat in on-shore facilities. Excessive amounts of either gluteraldehyde or MEA would yield a water phase that did not permit microbial growth.

Example 11

Neutralization of Biocides with Other Nitrogen Compounds

A series of different nitrogen-containing compounds were evaluated as materials to neutralize gluteraldehyde. For these experiments, 10:1 ratio of minimal media to n-$C_{16}$ were prepared, mixed with 10 ppm of gluteraldehyde (G) and evaluated in 250 ml flasks. The different nitrogen-containing compounds evaluated include the following:

Monoethanolamine (MEA)
Diethanolamine (DEA)
Methyldiethanolamine (MDEA)
Diethylamine (DA)

Aniline (A)

Two moles of each of the nitrogen-containing compound to gluteraldehyde were added to the flasks. Then 10 μl of the bacterial inoculum was added to each flask. The results are shown below in Table VII.

Control samples were also run with the nitrogen-containing compound and without the gluteraldehyde. These control samples permitted an assessment of the toxicity of the nitrogen-containing compound.

TABLE VII

Neutralization of Biocides with Nitrogen Compounds

| Time(days) | 0 | 1 | 2 | 6 | 7 | 9 | 13 | 20 |
|---|---|---|---|---|---|---|---|---|
| With MEA | − | − | − | + | + | + | + | + |
| MEA control | − | − | − | − | + | + | + | + |
| With DEA | − | + | + | + | + | + | + | + |
| DEA control | − | − | − | + | + | + | + | + |
| With MDEA | − | − | − | − | + | + | + | + |
| With diethylamine | − | − | − | + | + | + | + | + |
| Diethylamine control | − | − | − | + | + | + | + | + |
| With aniline | − | − | − | − | − | − | − | − |
| Control: no G/no amine | − | − | − | + | + | + | + | + |

These results show that MEA, DEA, MDEA and diethylamine are all effective in neutralizing 10 ppm of gluteraldehyde. Furthermore, these nitrogen-containing compounds are not excessively toxic themselves and permit microbial growth even in the absence of gluteraldehyde. In contrast, aniline is excessively toxic and does not permit microbial growth in experiments with or without gluteraldehyde.

Various modifications and alterations of this invention will become apparent to those skilled in the art without departing from the scope and spirit of this invention.

Example 12

Comparing the Acute Toxicity, to Larval Sheepshead Minnow (*Cyprinodon variegatus*), of Glutaraldehyde and Glutaraldehyde Neutralized with Mono-ethanolamine (MEA)

In a control experiment the acute toxicity of separate biocide (glutaraldehyde) and neutralizing agent (MEA) was measured in a 96 h static bioassay test (Methods for Measuring the Acute Toxicity of Effluent and Receiving Waters to Freshwater and Marine Organisms, 4$^{th}$ edition. EPA/600/4-90/027F Washington D.C. section 2.02, paragraph 1.) conducted at Pacific Eco-Risk Laboratories, Martinez, Calif. The results are summarized in the table below.

Acute Toxicity Measured on Larval Sheepshead Minnow (*Cyprinodon variegatus*)

| Compound | LC-50 (mg/L) | LOEC (mg/L) | NOEC (mg/L) |
|---|---|---|---|
| Glutaraldehyde | 26 | 25 | 13 |
| Monoethanolamine | 1500 | 1700 | 1000 |

LOEC is the Lowest Observable Effect Concentration and is defined as the minimum concentration where mortality is observed for the test species. NOEC is the No Observable Effect Concentration and is defined as the highest concentration tested where no mortality was observed in the test species. LC-50, the concentration that will cause mortality of 50% of the organisms tested within 96 h, is a calculated value based on all observations.

In a second experiment, the toxicity of glutaraldehyde in the presence and absence of MEA was measured and compared. Based on the results of the control experiment above, solutions having the concentrations of glutaraldehyde and MEA listed in the table below were prepared in the fish bioassay media provided by the testing laboratory. The solutions were mixed for 48 hours prior to the start of the bioassays. The solutions were diluted to perform bioassays at starting glutaraldehyde concentrations of 100, 50, 37.5, 25, and 10, 5 mg/L Acute Toxicity Measured on Larval Sheepshead Minnow (*Cyprinodon variegatus*)

| Glutaraldehyde (mg/L) | MEA (mg/L) | Glutaraldehyde: MEA Molar Ratio | LC50 (mg/L) |
|---|---|---|---|
| 100 | 0 | — | 25 |
| 100 | 62.5 | 1:1 | >100 |
| 100 | 125 | 1:2 | >100 |

The toxicity of glutaraldehyde alone was found to be the same as that determined the control experiment. Surprisingly no fish mortality was observed at any test concentrations where MEA was added. Consequently the LC50 for the neutralized biocide is greater than the maximum concentration test or 100 mg/L. This is consistent with the observations made on hydrocarbon degrading microorganisms. Thus water treated by such a technique would have significantly reduced toxicity when discharged into the environment.

What is claimed is:

1. A biologically inhibited hydrocarbonaceous product comprising:
    a) Fischer-Tropsch-derived liquid products subject to biological growth; and
    b) an effective amount of a deactivatable biocide to resist visible growth of micro-organisms for at least 10 days under ambient conditions when exposed to a certified inoculant,
   wherein the deactivatable biocide is irreversibly deactivated after the period in which biological growth is expected.

2. A product according to claim 1, wherein the Fischer-Tropsch products are selected from the group consisting of Fischer-Tropsch naphtha, Fischer-Tropsch jet fuel, Fischer-Tropsch diesel fuel, Fischer-Tropsch solvent, Fischer-Tropsch lube base stock, Fischer-Tropsch lube base oil, Fischer-Tropsch lube base oil feedstock and mixtures thereof.

3. A product according to claim 1, wherein the Fischer-Tropsch products have a branching index of less than five.

4. A product according to claim 1, wherein the biocide is selected from the group consisting of aldehydes, alkynes, and mixtures thereof.

5. A product according to claim 4, wherein the biocide is selected from the group consisting of glutaraldehyde, 1-hexyne, propargyl alcohol, and mixtures thereof.

6. A product according to claim 3 wherein the biocide is a Fischer-Tropsch-derived deactivatable biocide.

7. A method of inhibiting growth and reproduction of microorganisms in hydrocarbonaceous products containing minor amounts of water, comprising the steps of:
    a) providing a hydrocarbonaceous product;
    b) adding an effective amount of a deactivatable biocide to resist visible growth for at least 10 days under ambient conditions when exposed to a certified inoculant;

c) adding an effective amount of neutralizing agent to deactivate the biocide after the period in which growth and reproduction of microorganisms is expected.

8. A method according to claim 7, wherein the biocide is added at a concentration of less than 1 wt %.

9. A method according to claim 7, wherein the biocide is added at a concentration of less than 1000 ppm.

10. A method according to claim 9, wherein the biocide is added at a concentration of less than 100 ppm.

11. A method according to claim 7, wherein the biocide is an aldehyde and the neutralizing agent is a nitrogen-containing compound selected from the group consisting of amines, amino acids, amino alcohols, and mixtures thereof.

12. A method according to claim 7, wherein the biocide is an alkyne and the neutralizing agent is a hydrogenation catalyst and $H_2$.

13. A method according to claim 11, wherein the biocide is glutaraldehyde and the nitrogen-containing compound is monoethanolamine.

14. A method of inhibiting growth and reproduction of microorganisms in hydrocarbonaceous products containing minor amounts of aqueous liquids, comprising the steps of:
   a) providing a rapidly biodegradable hydrocarbonaceous product;
   b) adding an effective amount of a deactivatable biocide to resist visible growth for at least 10 days under ambient conditions when exposed to a certified inoculant; and
   c) adding an effective amount of a neutralizing agent to deactivate the biocide after the period in which growth and reproduction of microorganisms is expected.

15. A method according to claim 14, wherein the rapidly biodegradable hydrocarbonaceous product is Low Aromatics Diesel Fuel or Fischer Tropsch derived liquid hydrocarbonaceous product.

16. A method according to claim 14, further comprising a step d) separating the aqueous liquid from the hydrocarbonaceous product.

17. A method according to claim 16, wherein the separation step d) is performed after adding the neutralizing agent.

18. A method according to claim 16, wherein the separation step d) is performed after adding the neutralizing agent.

19. A method according to claim 16, further comprising a step e) treating the aqueous liquid in a biological oxidation facility to remove hydrocarbons.

20. A method according to claim 15, wherein the biocide is an alkyne and the neutralizing agent is a hydrogenation catalyst and $H_2$.

21. A method according to claim 15, wherein the biocide is glutaraldehyde and the neutralizing agent is monoethanolamine.

22. A method of inhibiting growth and reproduction of microorganisms in Fischer-Tropsch-derived liquid products, containing minor amounts of water, comprising the steps of:
   a) performing a Fischer-Tropsch synthesis process;
   b) isolating Fischer-Tropsch-derived liquid products from the Fischer-Tropsch process;
   c) isolating Fischer-Tropsch-derived deactivatable biocides from the Fischer-Tropsch process;
   d) mixing the Fischer-Tropsch-derived liquid products with an effective amount of the Fischer-Tropsch-derived biocide to resist visible growth for at least 10 days under ambient conditions when exposed to a certified inoculant; and
   e) adding an effective amount of neutralizing agent to deactivate the biocide after the period in which biological growth is expected.

23. The method according to claim 22, wherein the Fischer-Tropsch derived deactivatable biocides are isolated by distillation or chromatographic separation.

24. The method according to claim 22, further comprising a step f) separating the water from the hydrocarbonaceous product.

25. The method according to claim 24, further comprising a step g) treating the water in a biological oxidation facility to remove hydrocarbons.

26. A method according to claim 22, wherein the biocide is an alkyne and the neutralizing agent is a hydrogenation catalyst and $H_2$.

27. A method according to claim 22, wherein the biocide is glutaraldehyde and the neutralizing agent is monoethanolamine.

28. A method of inhibiting growth and reproduction of microorganisms in Fischer-Tropsch-derived liquid products containing minor amounts of water, comprising the steps of:
   a) performing Fischer-Tropsch synthesis on syngas to provide a product stream;
   b) fractionally distilling the product stream and isolating liquid hydrocarbonaceous products and oxygenates;
   c) subjecting the oxygenates to oxidation to form aldehydes;
   d) blending the liquid hydrocarbonaceous products with an effective amount of the aldehydes to resist visible growth for at least 10 days under ambient conditions when exposed to a certified inoculant;
   e) adding an effective amount of neutralizing agent to deactivate the aldehydes after the period in which biological growth is expected.

29. A method according to claim 28, wherein the aldehydes are glutaraldehyde and the neutralizing agent is monoethanolamine.

30. A method according to claim 28, wherein the oxygenates are isolated from light Fischer Tropsch products.

31. A method according to claim 28, wherein the oxygenates are isolated from waste-water generated as part of the Fischer-Tropsch process.

32. A method of inhibiting growth and reproduction of microorganisms in Fischer-Tropsch-derived liquid products containing minor amounts of water, comprising the steps of:
   a) performing Fischer-Tropsch synthesis on syngas to provide a product stream;
   b) fractionally distilling the product stream and isolating liquid hydrocarbonaceous products and olefins;
   c) subjecting the olefins to dehydrogenation to form alkynes;
   d) blending the liquid products with an effective amount of the alkynes to resist visible growth for at least 10 days under ambient conditions when exposed to a certified inoculant;
   e) adding an effective amount of neutralizing agent to deactivate the alkynes after the period in which biological growth is expected.

33. A method according to claim 32 wherein the alkynes are primary alkynes and the neutralizing agent is a hydrogenation catalyst and $H_2$.

34. A method according to claim 32, wherein the olefins are formed from a thermal cracking process which uses a heavy Fischer Tropsch feed derived from a Fischer Tropsch process.

35. A method according to claim 32, wherein the olefins are isolated from light Fischer Tropsch products.

* * * * *